(12) United States Patent
Keinan et al.

(10) Patent No.: US 6,500,957 B1
(45) Date of Patent: Dec. 31, 2002

(54) STABLE DIHYDRIDOALKYL PLATINUM(IV) COMPLEX, METHODS OF PRODUCING SAME AND UTILIZING SAME

(75) Inventors: Ehud Keinan, Timrat (IL); Ariel Haskel, San Diego, CA (US)

(73) Assignee: Technion Research and Development Foundation Ltd., Haifa (IL)

( * ) Notice: Subject to any disclaimer, the term of this patent is extended or adjusted under 35 U.S.C. 154(b) by 0 days.

(21) Appl. No.: 10/030,917

(22) PCT Filed: Jul. 13, 2000

(86) PCT No.: PCT/IL00/00415
§ 371 (c)(1),
(2), (4) Date: May 16, 2002

(87) PCT Pub. No.: WO01/05208
PCT Pub. Date: Jan. 25, 2001

Related U.S. Application Data

(60) Provisional application No. 60/144,045, filed on Jul. 16, 1999.

(51) Int. Cl.[7] ............................. C07F 15/00; C07F 5/02; B01J 31/00
(52) U.S. Cl. ........................ 548/101; 548/110; 556/6; 556/136; 502/155; 568/881
(58) Field of Search .................. 556/8, 136; 548/101, 548/110; 502/155; 568/881

(56) References Cited

U.S. PATENT DOCUMENTS 5,627,164 A * 5/1997 Gorun et al. .................. 514/64
6,150,529 A * 11/2000 Wang et al. ................. 548/101

OTHER PUBLICATIONS

Giustiniani et al., Reduction of olefins by Means of an HA–Platinum(II) Hydride System, Inorganic Chemistry, May 1969, vol. 8, No. 5, pp. 1048–1051.*
Roundhill et al., Some New Platinum Acetylene complexes, Chemical Communications, Oct. 2, 1968, No. 20, pp. 1233–1234.*
Stall et al., Investigations of the Factors Affecting the Stability of Dihydrogen Adducts of Platinum(II), Inorganic Chemistry, May 18, 1998, vol. 37, No. 10, pp. 2422–2431.*

* cited by examiner

Primary Examiner—Porfirio Nazario-Gonzalez
(74) Attorney, Agent, or Firm—G. E. Ehrlich Ltd.

(57) ABSTRACT

A platinum complex is described to include a platinum(IV) metal center so positioned and oriented in the complex so as to complex in cis orientations with two hydride groups and with an alkyl group.

19 Claims, 5 Drawing Sheets

STABLE DIHYDRIDOALKYL PLATINUM(IV) COMPLEX, METHODS OF PRODUCING SAME AND UTILIZING SAME

CROSS-REFERENCE TO RELATED APPLICATIONS

This application is a National Stage Application under 35 U.S.C. §371 of International Application No. PCT/IL00/00415, filed Jul. 13, 2000, which claims the benefit of U.S. Provisional Application No. 60/144,045, filed Jul. 16, 1999.

FIELD AND BACKGROUND OF THE INVENTION

The present invention relates to a novel platinum(IV), herein also Pt(IV) or $Pt^{IV}$, complex and, more particularly, to a dihydroalkyl Pt(IV) complex, a method of producing same and a method of utilizing same in catalysis involving hydrocarbon activation and in reduction of organic molecules and of water to produce dihydrogen.

The direct, selective oxidation of alkanes has long been a major challenge in transition metal chemistry [1]. The Shilov system, which employs chloroplatinum salts in aqueous media to catalytically functionalize methane, has been the subject of a number of mechanistic studies over the past few years [2]. Unfortunately, unlike the classical Shilov system, most of the organometallic models used for these studies are extremely air- and moisture-sensitive. A key intermediate in this process was proposed to be an alkyl(hydrido)metal complex. Attempts to prepare such complexes under aqueous conditions resulted in platinum(IV)hydroxo complexes with concomitant release of hydrogen gas, probably via rapid hydrolysis of short-lived platinum(IV)hydrido intermediates [3,4]. Consequently, most of the known hydrido (alkyl)platinum(IV) complexes were prepared and studied in the absence of oxygen and under anhydrous conditions. The dihydrido(alkyl)platinum(IV) complexes seemed to be more elusive than either the hydrido(alkyl)platinum(IV) or the dihydrido(dihalo)platinum(IV) complexes [5]. Bercaw and coworkers, who studied extensively the individual steps of the catalytic oxidation of alkanes [6], have recently proposed a dihydrido(alkyl)platinum(IV) complex as a hypothetical intermediate in the low-temperature protonolysis of $(PCy_3)_2Pt(H)R$ ($R=CH_3$, Ph) which produced methane or benzene [7].

While reducing the present invention to practice a stable dihydrido(methyl)platinum(IV) complex, $TpPtH_2Me$, 1 (Tp=hydridotris(Pyrazolyl)borate) was prepared via the reaction of TpPtMeCO, 2, with water. The resultant complex, 1, was unexpectedly found to be air- and moisture-stable and was found to contain not only two cis hydride ligands but also a cis methyl ligand.

SUMMARY OF THE INVENTION

A novel, air- and moisture-stable dihydrido(methyl) platinum(IV) complex, $TpPtH_2Me$, 1 (Tp=hydridotris (pyrazolyl)borate) is formed as the sole product by the reaction of TpPMeCO, complex 2, with water. Complex 1 was structurally characterized by elemental analysis, $^1H$-NMR, $^{13}C$-NMR, and FTIR Without being bound to any specific theory, the proposed mechanism of the reaction of complex 2 and water involves an initial nucleophilic attack by a water molecule on the coordinated carbonyl in 2 with subsequent release of $CO_2$ followed by protonation at the platinum center to produce complex 1. The resultant complex, 1, was unexpectedly found to be air- and moisture-stable and was found to contain not only two cis hydride ligands but also a cis methyl ligand.

Thus, according to one aspect of the present invention there is provided a platinum complex comprising a platinum (IV) metal center so positioned and oriented in the complex so as to complex in cis orientations with two hydride groups and with an alkyl, e.g., methyl, group, which complex can be in a solid state, e.g., crystallized, or dissolved as a portion of a solution.

According to another aspect of the present invention there is provided a solution comprising a solvent and a platinum complex therein in which a platinum(IV) metal center is complexed in cis orientations with two hydride groups and with an alkyl group.

According to yet another aspect of the present invention there is provided a method of preparing a platinum complex including a platinum(IV) metal center so positioned and oriented so as to complex in cis orientations with two hydride groups and with an alkyl group, the method comprising the step of contacting a platinum complex including a platinum(II) metal center being complexed with a CO group and the alkyl group and with water to thereby obtain the platinum complex including the platinum(IV) metal center so positioned and oriented so as to complex in cis orientations with the two hydride groups and with the alkyl group.

According to further features in preferred embodiments of the invention described below, the complex including said platinum(II) metal center complexed with the CO group and the alkyl group includes a nitrogen based polydentate ligand such as, but not limited to, hydridotris(pyrazolyl) borate, hydridotris(pyrazolyl) methane, aryltris(pyrazolyl) borate, aryltris(pyrazolyl) methane, heteroaryltris(pyrazolyl) borate, heteroaryltris(pyrazolyl) methane, alkyltris (pyrazolyl) borate and substitutes thereof, which serve as a complexing ligand (agent).

According to still another aspect of the present invention there is provided a process of activating a C—C and/or a C—H bond of a hydrocarbon, the process comprising the step of contacting the hydrocarbon with a platinum complex including a platinum(IV) metal center so positioned and oriented in the complex so as to complex in cis orientations with two hydride groups and with an alkyl group, thereby activating the C—C and/or a C—H bond of the hydrocarbon.

According to further features in preferred embodiments of the invention described below, the platinum complex includes hydridotris(pyrazolyl) borate, hydridotris (pyrazolyl) methane, aryltris(pyrazolyl) borate, aryltris (pyrazolyl) methane, heteroaryltris(pyrazolyl) borate, heteroaryltris(pyrazolyl) methane, alkyltris(pyrazolyl) borate and substitutes thereof.

According to still further features in the described preferred embodiments the hydrocarbon and the complex are in solution, the solution includes at least one substance selected from the group consisting of water, an alcohol, a ketone, aldehyde, an organic acid or any other organic molecule.

According to still further features in the described preferred embodiments the hydrocarbon is selected from the group consisting of an alkane, an alkene, an alkyne and an arene. Other hydrocarbons are also suitable, such as functionalized hydrocarbons.

The present invention successfully addresses the shortcomings of the presently known configurations by providing a novel platinum(IV) metal center complex characterized by cis orientated coordinative bonds with two hydride groups and with an alkyl group, which is both moisture and air stable and which can, therefore, be advantageously used for activating hydrocarbon C—C and/or C—H bonds and for reduction of organic molecules and of water to produce dihydrogen, for the production of a variety of useful chemicals

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
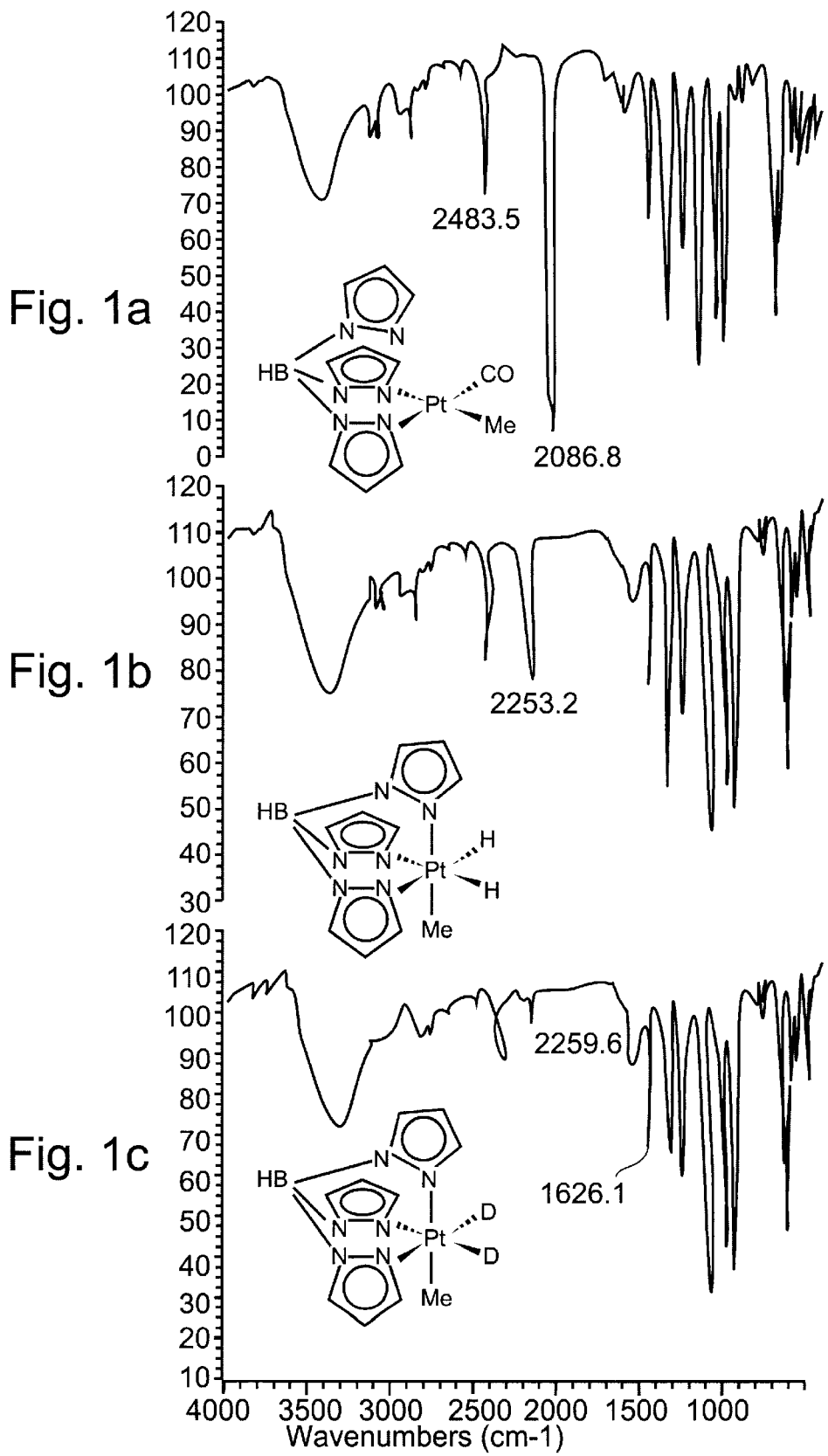
FIGS. 1a–c presents structures and IR spectra of TpPtMeCO (1a), TpPtMeH$_2$ (1b), and TpPtMeD$_2$ (1c).

The present invention is of a novel platinum(IV), herein also Pt(IV) or Pt$^{IV}$, complex characterized by cis orientated coordinative bonds with two hydride groups and with an alkyl group, which is both moisture and air stable and which can, therefore, be advantageously used for activating hydrocarbon C—C and/or C—H bonds and for reduction of organic molecules and water, for the production of a variety of useful chemicals. The reduction of water in accordance with the teachings of the present invention is effected by CO so as to obtain dihydrogen and CO$_2$ in a reaction known as water-gas shift (WGS). The present invention is further of a method of producing the novel Pt(IV) complex.

The structure and operation of a Pt(IV) complex according to the present invention may be better understood with reference to the drawings and accompanying descriptions and examples.

Before explaining at least one embodiment of the invention in detail, it is to be understood that the invention is not limited in its application to the details of construction and the arrangement of the components set forth in the following description or illustrated in the drawings or the examples that follows. The invention is capable of other embodiments or of being practiced or carried out in various ways. Also, it is to be understood that the phraseology and terminology employed herein is for the purpose of description and should not be regarded as limiting.

While reducing the present invention to practice, a novel alkyl dihydride complex, TpPtMeH$_2$, 1, was formed as the sole product by the reaction of TpPtMeCO with water under air. It is propose that the formation of this product involves an initial nucleophilic attack by a water molecule on the coordinated carbonyl followed by the release of CO$_2$ to produce a TpPtHMe intermediate, which undergoes protonation at the platinum center to produce complex 1.

According to one aspect of the present invention there is provided a platinum complex which includes a platinum(IV) atom, so positioned and oriented in the complex, so as to complex in cis orientations with two hydride groups and with an alkyl, e.g., methyl, group. The complex according to the present invention may be in a solid state, e.g., crystallized, or dissolved as a portion of a solution. As has already been mentioned, an unexpected and certainly unique characteristic of the Pt complex of the present invention is that both the hydride and the alkyl groups are complexed thereto is all cis orientations. The formation of such Pt complexes was never attempted because they were though to be highly unstable, short lived and therefore not useful.

The preparation of a Pt(IV) complex according to the present invention involves contacting a platinum complex including a platinum(II) metal center which is complexed with a CO group and an alkyl group with water to thereby obtain the novel and advantageous platinum(IV) complex of the present invention. As is further detailed in the Examples section that follows, this process occurs at ambient temperature under oxidizing environment (in air) and results in high yields of the novel complex.

A suitable reactant in this reaction in a Pt(II) complex which includes hydridotris(pyrazolyl) borate coordinatively bound to the Pt(II) atom. Other complexing ligands, such as but not limited to, hydridotris(pyrazolyl) methane, aryltris (pyrazolyl) borate, aryltris(pyrazolyl) methane, heteroaryltris(pyrazolyl) borate, heteroaryltris(pyrazolyl) methane and alkyltris(pyrazolyl) borate, all characterized by being apt of coordinating a metal, such as Pt(II), in more than one fashion. Hence, the reactant complex may adopt either a tetra or penta coordinated geometry (e.g., trigonal, bipyramid, square pyramid, square planar, tetrahedral and tetragonal) around the metal center, can be used as substitutes to hydridotris(pyrazolyl) borate. Thus, the resulting novel Pt(IV) complex includes, as a complexing ligand, hydridotris(pyrazolyl) borate, hydridotris(pyrazolyl) methane, aryltris(pyrazolyl) borate, aryltris(pyrazolyl) methane, heteroaryltris(pyrazolyl) borate, heteroaryltris (pyrazolyl) methane, alkyltris(pyrazolyl) borate or a substituent thereof.

According to still another aspect of the present invention there is provided a process of activating a C—C and/or a C—H bond of a hydrocarbon. The process according to this aspect of the present invention involves contacting the hydrocarbon with a platinum complex including a platinum (IV) metal center so positioned and oriented in the complex so as to complex in cis orientations with two hydride groups and with an alkyl group, thereby activating the C—C and/or a C—H bond of the hydrocarbon.

The hydrocarbon and the complex are in solution, the solution preferably includes at least one additional substance, such as, but not limited to, water, an alcohol (e.g., ethanol, methanol, propyl alcohol, isopropyl alcohol and longer chain alcohols including 4–15 carbons in a branched or linear chain), a ketone (such as acetone), an aldehyde and/or an organic acid, such as acetic acid and any type of organic molecule containing for example at least one multiple bond.

The hydrocarbon can be, for example, an alkane, such as methane, ethane, propane, butane, pentane, hexane, heptane, etc., an alkene, such as ethylene, propene, butene, pentene, hexene or any heteroalkene, an alkyne, such as acetylene, 1-propyene, 2-propyene, 2-butyne or 3-butyne, or an arene, such as benzene or functionalized phenyl. In one specific example, the hydrocarbon is methane, which is used to produce methanol as an alternative to the so called Shilov[2] process, using the novel Pt(IV) complex of the present invention. Other examples include the oxidation of benzene to phenol and of alkenes and alkynes to the corresponding alcohols.

According to another aspect of the invention there is provided a process of reducing an organic molecule or water. The process according to this aspect of the invention is effected by contacting the organic molecule or water with a platinum complex including a platinum(IV) metal center so positioned and oriented in the complex so as to complex in cis orientations with two hydride groups and with an alkyl group, thereby reducing the organic molecule or water.

Thus, the present invention provides a novel platinum(IV) complex characterized by cis orientated coordinative bonds with two hydride groups and with an alkyl group, which is both moisture and air stable and which can, therefore, be advantageously used for activating hydrocarbon C—C and/or C—H bonds or reducing organic molecules or water for the production of a variety of useful chemicals.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Preparation of Complex 1

Complex 2[8] (10 mg, 0.022 mmol) was dissolved in acetone-$H_2O$ (1:1, 0.5 mL) and the mixture was kept at room temperature for 24 h. The white precipitate (6.9 mg, 0.016 mmol, 73%) was collected and dried under reduced pressure, and then analyzed by elemental analysis [9], $^1$H-NMR, $^{13}$C-NMR, and FTIR. The same result was obtained under either air or argon atmosphere.

Example 2

$^1$H-NMR Analysis of Complex 1

In addition to the Pt-Me signal at 1.04 ppm ($^2J_{Pt-H}$=65.4 Hz, 3H) in the $^1$H-NMR spectrum, a 2:1 ratio of all pyrazolyl signals was observed, indicating a symmetrical structure of complex 1, with two identical and one different pyrazolyl rings. The fact that both the H3 and H3' pyrazolyl hydrogens exhibited platinum satellites confirmed that all three pyrazolyl rings were attached to the platinum metal. A diagnostic $Pt^{IV}$-H signal at –20.04 ppm ($^1J_{Pt-H}$=1276 Hz, 2H) was consistent with two hydride ligands [10].

In order to rule out a non-classical conformation of 1 ($\eta^2$-$H_2$), a $T_1$ temperature-dependence experiment was carried out in acetone-$d_6$. Complex 1 exhibited a minimal value of $T_1$ (748 ms) at –70° C. which characterizes classical hydride ligands [11].

Example 3

$^{13}$C-NMR Analysis of Complex 1

The $^{13}$C-NMR spectrum of complex 1[12] showed a remarkably high-field Pt-$CH_3$ signal at –30.4 ppm ($^1J_{Pt-C}$=561.5 Hz)[13]. The C3 and C3' carbon signals at 141.0 ppm ($^2J_{Pt-C}$=27.3 Hz, 2C) and at 144.5 ppm ($^2J_{Pt-C}$=35.3 Hz, 1C) reflected once again the above mentioned symmetry of complex 1 with all three pyrazolyl groups being attached to the platinum atom. A similar conclusion could be drawn from the C4 and C4' carbon signals whose intensities showed approximately a 2:1 ratio. By contrast, C5 and C5' overlapped to form a broad signal.

Example 4

Infrared Spectroscopy of Complex 1

Infrared spectroscopy was particularly useful for the structure determination of complex 1 (FIGS. 1a–c). Complex 2 was characterized by a very strong CO signal at 2087 $cm^{-1}$ (FIG. 1a). This signal was missing in 1 (FIG. 1b), which exhibited a strong $Pt^{IV}$-H signal at 2253 $cm^{-1}$ [14]. Furthermore, when 2 was reacted with acetone-$d_6$/$D_2O$ this platinum-hydride absorption was shifted to 1626 $cm^{-1}$, as expected for a platinum-deuteride complex (FIG. 1c)[15].

The mechanistic details by which complex 1 was formed are of special importance because, as is further described and discussed hereinbelow, they can provide valuable information about two key transformations in organometallic chemistry: C—H activation with transition metals and the WGS reaction [16]. It is likely that introduction of the two hydride ligands occur via two different mechanistic steps: a) a nucleophilic attack by a water molecule on the coordinated carbonyl followed by release of $CO_2$ as is known for the WGS reaction; and b) oxidative addition of a water molecule (protonation of the platinum metal).

Example 5

Variable Temperature NMR Analysis of Complex 2

Figure 2:
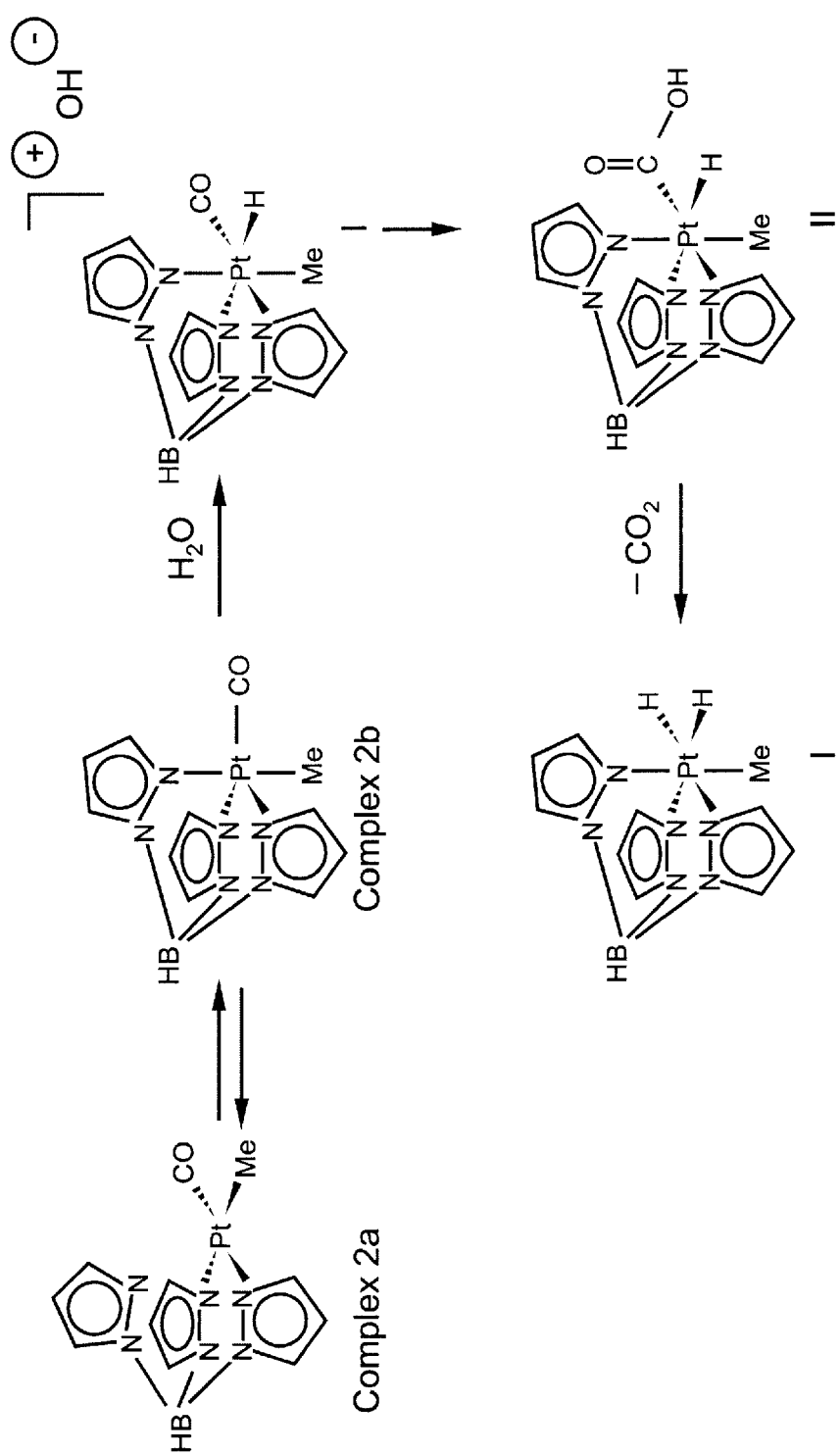
FIG. 2 present the chemical formation of complex 1 according to the present invention by interaction of complex 2 (equilibrium between 2a and 2b) with water.

Variable temperature NMR experiments have indicated that complex 2 in $CDCl_3$ solution is fluxional at room temperature [17], but adopts a trigonal bipyramide geometry, 2a, at low temperatures. In the solid state, however, the molecule takes up a square planar geometry, 2b, with the Tp group becoming a bidentate ligand [18]. The fluxional behavior of 2 is apparent from its $^1$H NMR spectral data [19]. The trigonal bipyramide geometry of 2 at low temperature (–40° C.) is secured by $^{13}$C NMR spectra, which show platinum coupling to all C-3 pyrazole rings [20]. Therefore it is herein suggested, in a non-limiting fashion, that in solution, 2a and 2b coexist in equilibrium (FIG. 2). Another indicator for the hapicity of the Tp ligand is the nature of the B-H bond as reflected by $^{11}$B NMR[21] and by IR[22]. The IR spectra of complex 2 was measured in solution ($v_{B-H}$=2460 cm$^{-1}$) and in the solid state ($v_{B-H}$=2483.5 cm$^{-1}$, FIGS. 1a–c) and observed a significantly broader B-H stretch signal in the former. These results are consistent with equilibrium between 2a and 2b in solution.

Without being limited to any specific theory, it is herein proposed that the first step in the reaction between complex 2 and water (FIG. 2) involves a nucleophilic attack by a water molecule on the coordinated carbonyl to produce the acyl intermediate [17]. This intermediate can release a molecule of carbon dioxide to produce intermediate II. To verify this WGS-type mechanism an isotopically labeled complex, TpPtMe$^{13}$CO, was prepared and its reaction with a 1:1 mixture of acetone-d$_6$ and D$_2$O using $^{13}$C-NMR spectroscopy was followed. It was found that the carbonyl signal of 2 at 164.70 ppm ($^1J_{Pt-C}$=1880 Hz) disappeared slowly with concomitant appearance of a new singlet at 125 ppm (with no coupling to Pt)[23]. The assignment of the latter signal to free $^{13}$CO$_2$ was confirmed by the fact that the intensity of this signal was diminished substantially upon either purging the sample with argon or by applying a partial vacuum.

The final step of the proposed reaction involves direct protonation of either II or its pentacoordinated isomer III to produce 1 (FIG. 2). This step is probably facilitated by the presence of carbonic acid (aqueous CO$_2$), which was produced in the previous step. An analogous transformation was recently reported by Canty and coworkers who used acidic reagents, including acetic acid, HBF$_4$ and phenol, to convert TpPtMe$_2^-$ to TpPtMe$_2$(H)[24]. Similarly, Templeton and coworkers have used HCl to transform Tp'PtMe$_2^-$ to Tp'PtMe$_2$(H), (Tp'=hydridotris(3,5-dimethyl(pyrazolyl)borate)[25]. The oxidative addition of protic acids to platinum (II) complexes represents a common entry to hydridoplatinum(IV) complexes [26].

Example 6

Identifying the Preferred Protonation Site in Complex 2 and Production of Complex 3

Figure 3:
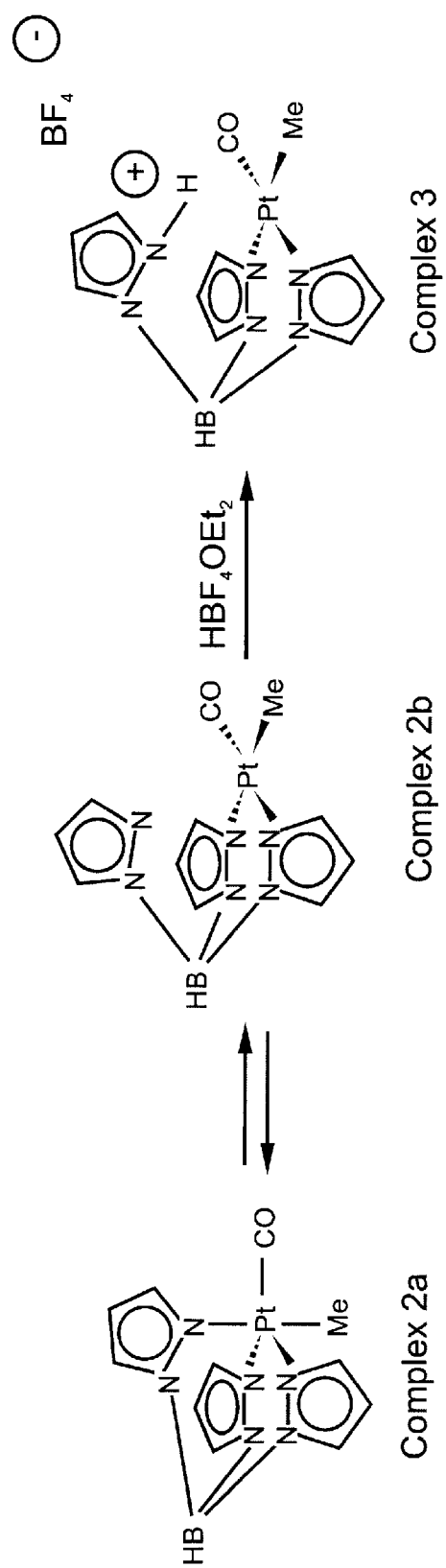
FIG. 3 is a scheme demonstrating the formation of complex 3 according to the present invention. Complex 3 is formed by reacting complex 2 with a strong acid, such as HBF$_4$OE$_{t2}$
Figure 4:
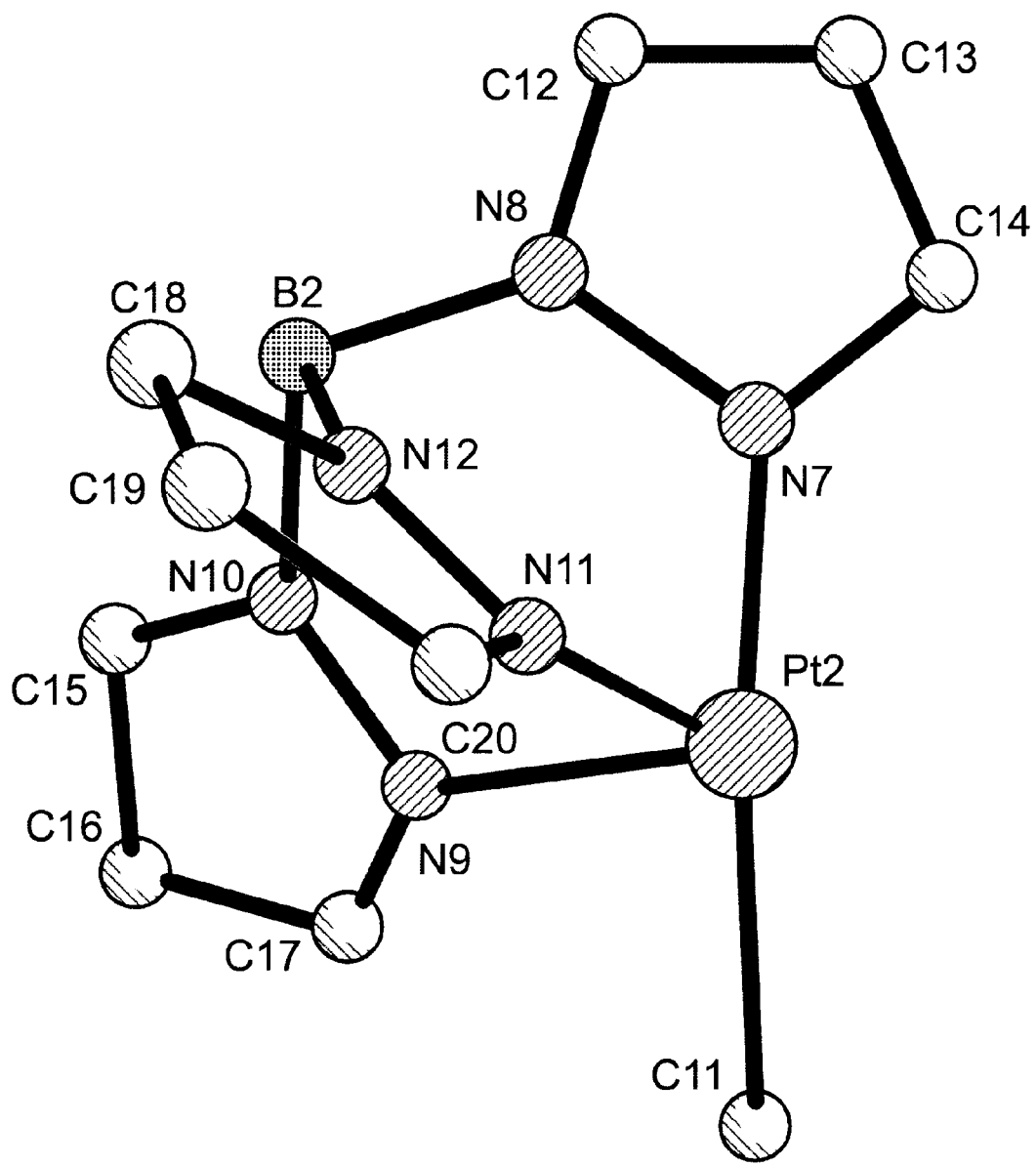
FIG. 4 presents the molecular structure of complex 3 with the adopted atom numbering (only one of the two molecules of the unit cell is shown). Important distances (Angstrom) include: Pt1—N1=2.050 (14), Pt1—N4=2.075 (13), Pt1—C1=1.80 (3), Pt1—C2=2.08 (2). Some relevant angles (deg): N1—Pt1—N4=88.7 (5), N1Pt1—C2=88.6 (7), N4—Pt1—C1=94.7 (9), C2—Pt1—C1=88.1 (10).

Since no clear experimental evidence was available for the relative timing of the WGS and protonation steps, the preferred protonation site in complex 2 was examined. Thus, reaction of 2 (10 mg, 0.022 mmol) with HBF$_4$ether (0.0031 mL, 1 equiv) in either ether (2 mL) or in acetone-water (1:1, 1 mL) produced the tetrafluoroborate salt 3 (FIG. 3) in quantitative yield (12.0 mg, 0.022 mmol)[27]. Complex 3 was recrystallized from CH$_2$Cl$_2$-hexane at 4° C. and analyzed by X-ray crystallography (FIG. 4)[28]. As can be clearly concluded from the solid state structure of 3, the preferred protonation site in 2 is one of the pyrazolyl rings and not the platinum center. This observation supports the assumption that the initial step in the conversion of 2 to 1 is probably a WGS-type step (FIG. 2) and not protonation at the metal center. Tables of complete crystallographic data for complex 3 is available, free of charge, via the Internet at http://pubs.acs.org.

Example 7

X-ray Crystallography and Difraction Analysis of Complex 1

Crystals of complex 1 were grown from a 1:1 mixture of acetone-water at 25° C. and analyzed by X-ray crystallography [29]. The solid state structure of complex 1 was revealed with a low R$_f$ value of 7.4% and confirmed its above described spectroscopy-elucidated structure.

A colorless thin plate of the compound was mounted on the Nonius Kappa CCD diffractometer with the φ axis almost parallel to the plate plane. Accurate cell parameters were obtained from 56367 reflections using MoKα. radiation. Data collection was performed with φ scans and a scans to fill in the Ewald Sphere. The crystal to detector distance was increased to 6.0 cm to improve resolution between diffraction spots. Numerical absorption corrections were applied to the intensities after the crystal shape was accurately defined.

The complex Pt atomic positions were located by direct methods and the light atoms by successive Fourier difference maps. The structure was refined anisotropically for the Pt atoms and isotropically for the light atoms but refinement at this stage gave very unsatisfactory discrepancy factor R=0.176. Residual electron densities were totally meaningless regarding any additional chemical moieties but molecular packing was found quite reasonable. After some effort, a twinning model was suggested based on the proximity of the cell angle β to 90 deg. A twin law -I 0 0 0 I 0 0 0 I was introduced into the least squares routine and after four cycles, the R factor dropped from 0.176 to 0.073. Refinement gave a twin component of 0.277(3) indicating that the crystal is a composite of 78% of one component and 22% of a second component with it's a̲ axis reversed. Here, the twin model was found successful because splitting between spots from each of the components was rather small and allowed spot integration of both contributions. Residual electron density of 3.78 e.A$^{-3}$ found around the Pt atom was attributed to absorption effect. The programs used for data processing and refinement were: Data collection: Kappa CCD Server Software; Cell refinement and data reduction: DENZO-SMN Structure solution and refinement: SHELXL97. Molecular graphics: TEXSAN 1.6f: Software used to prepare material for publication: SHELXL97.

The results of the X ray analysis are presented in Tables 1–3 below.

TABLE 1

Crystal data and structure refinement for complex 1

| Identification code | Complex 1 |
|---|---|
| Empirical formula | C10 H15 B N6 Pt |
| Formula weight | 425.18 |
| Temperature | 293(2) K |
| Wavelength | 0.71073 A |
| Crystal system, space group | Monoclinic, P21/c |
| Unit cell dimensions | a = 7.790(2) A   alpha = 90 deg. |
| | b = 13.342(3) A   beta = 90.20(3) deg. |
| | c = 26.078(5) A   gamma = 90 deg. |
| Volume | 2710.2(11) A$^3$ |
| z, Calculated density | 8, 2.084 Mg/m$^3$ |
| Absorption coefficient | 10.346 mm$^{-1}$ |
| F(OOO) | 1600 |
| Crystal size | 0.02 × 0.24 × 0.24 mm |
| Theta range for data collection | 1.56 to 22.99 deg. |
| Limiting indices | O ≦ h ≦ 8, O ≦ k ≦ 14, −26 ≦ 1 ≦ 28 |
| Reflections collected/unique | 3120/3120 [R(int) = 0.0000] |
| Completeness to theta = 22.99 | 82.5% |
| Refinement method | Full-matrix least-squares on F$^2$ |
| Data/restraints/parameters | 3120/0/157 |
| Goodness-of-fit on F$^2$ | 1.077 |
| Final R indices [I > 2sigma(I)] | R1 = 0.0735, wR2 = 0.2046 |
| R indices (all data) | R1 = 0.0937, wR2 = 0.2101 |
| Largest diff. peak and hole | 3.778 and −1.664 e.A$^{-3}$ |

TABLE 2

Atomic coordinates ($\times 10^4$) and equivalent isotropic displacement parameters ($\text{Å}^2 \times 10^3$) for complex 1. U (eq) is defined as one third of the trace of the orthogonalized Uij tensor.

|       | x         | y        | z         | U (eq)  |
|-------|-----------|----------|-----------|---------|
| Pt(1) | 6989(2)   | 5763(1)  | −1575(1)  | 69(1)   |
| B(1)  | 7250(40)  | 8020(30) | −2061(12) | 52(9)   |
| N(1)  | 6020(30)  | 7100(18) | −1264(8)  | 51(6)   |
| N(2)  | 6390(30)  | 7992(19) | −1527(9)  | 52(6)   |
| N(3)  | 9150(30)  | 7569(18) | −1953(8)  | 48(6)   |
| N(4)  | 9290(40)  | 6560(20) | −1715(11) | 82(9)   |
| N(5)  | 5940(40)  | 6310(20) | −2320(10) | 76(8)   |
| N(6)  | 6310(30)  | 7254(19) | −2406(9)  | 55(7)   |
| C(1)  | 7850(60)  | 4400(30) | −1882(16) | 113(13) |
| C(2)  | 5100(30)  | 7360(20) | −850(10)  | 40(7)   |
| C(3)  | 4780(40)  | 8300(20) | −857(11)  | 48(8)   |
| C(4)  | 5570(40)  | 8690(20) | −1263(11) | 53(8)   |
| C(5)  | 10970(40) | 6440(20) | −1729(11) | 63(9)   |
| C(6)  | 11810(50) | 7320(30) | −1899(12) | 75(9)   |
| C(7)  | 10780(40) | 7920(30) | −2036(11) | 60(9)   |
| C(8)  | 5650(40)  | 7520(30) | −2884(12) | 62(9)   |
| C(9)  | 4910(50)  | 6610(30) | −3016(15) | 82(11)  |
| C(10) | 5050(40)  | 5940(30) | −2684(13) | 66(9)   |
| Pt(2) | 8001(2)   | 6547(1)  | 756(1)    | 66(1)   |
| C(11) | 7300(90)  | 5360(60) | 330(20)   | 220(30) |
| B(2)  | 7490(30)  | 8960(30) | 490(12)   | 47(9)   |
| N(7)  | 8900(30)  | 7824(18) | 1219(8)   | 48(6)   |
| N(8)  | 8470(30)  | 8679(17) | 1036(8)   | 45(6)   |
| N(9)  | 8800(30)  | 7372(19) | 71(9)     | 51(6)   |
| N(10) | 8510(20)  | 8394(16) | 79(6)     | 41(6)   |
| N(11) | 5590(30)  | 7382(18) | 659(9)    | 46(6)   |
| N(12) | 5750(30)  | 8357(17) | 537(8)    | 46(6)   |
| C(12) | 9100(40)  | 9410(20) | 1379(10)  | 47(7)   |
| C(13) | 9840(50)  | 8920(30) | 1792(16)  | 97(13)  |
| C(14) | 9580(40)  | 7930(30) | 1658(13)  | 73(10)  |
| C(15) | 9190(40)  | 8840(20) | −345(11)  | 58(8)   |
| C(16) | 9850(50)  | 7980(30) | −577(15)  | 86(11)  |
| C(17) | 9710(40)  | 7210(30) | −331(12)  | 62(9)   |
| C(18) | 4120(40)  | 8750(20) | 520(11)   | 52(8)   |
| C(19) | 3030(50)  | 7970(30) | 572(13)   | 86(10)  |
| C(20) | 3840(40)  | 7120(30) | 637(11)   | 63(9)   |

TABLE 3

Bond lengths [Å] and angles [deg] for complex 1

Angle Degree:

| Pt(1)-C(1)  | 2.10(5)  |
|-------------|----------|
| Pt(1)-N(1)  | 2.10(2)  |
| Pt(1)-N(4)  | 2.12(3)  |
| Pt(1)-N(5)  | 2.22(3)  |
| B(1)-N(6)   | 1.54(4)  |
| B(1)-N(2)   | 1.55(4)  |
| B(1)-N(3)   | 1.62(4)  |
| N(1)-C(2)   | 1.34(3)  |
| N(1)-N(2)   | 1.40(3)  |
| N(2)-C(4)   | 1.32(3)  |
| N(3)-C(7)   | 1.37(4)  |
| N(3)-N(4)   | 1.48(4)  |
| N(4)-C(5)   | 1.32(4)  |
| N(5)-C(10)  | 1.27(4)  |
| N(5)-N(6)   | 1.32(3)  |
| N(6)-C(8)   | 1.39(4)  |
| C(2)-C(3)   | 1.27(4)  |
| C(3)-C(4)   | 1.33(4)  |
| C(5)-C(6)   | 1.41(4)  |
| C(6)-C(7)   | 1.19(4)  |
| C(8)-C(9)   | 1.38(5)  |
| C(9)-C(10)  | 1.25(4)  |
| Pt(2)-C(11) | 2.01(8)  |
| Pt(2)-N(9)  | 2.19(2)  |
| Pt(2)-N(11) | 2.20(2)  |
| Pt(2)-N(7)  | 2.20(2)  |
| B(2)-N(10)  | 1.53(4)  |
| B(2)-N(12)  | 1.58(4)  |
| B(2)-N(8)   | 1.66(4)  |
| N(7)-C(14)  | 1.27(4)  |
| N(7)-N(8)   | 1.28(3)  |
| N(8)-C(12)  | 1.40(3)  |
| N(9)-C(17)  | 1.29(3)  |
| N(9)-N(10)  | 1.38(3)  |
| N(10)-C(15) | 1.37(3)  |
| N(11)-N(12) | 1.34(3)  |
| N(11)-C(20) | 1.41(4)  |
| N(12)-C(18) | 1.37(4)  |
| C(12)-C(13) | 1.38(5)  |
| C(13)-C(14) | 1.38(5)  |
| C(15)-C(16) | 1.40(5)  |
| C(16)-C(17) | 1.22(5)  |
| C(18)-C(19) | 1.34(5)  |
| C(19)-C(20) | 1.31(4)  |
| C(1)-Pt(1)-N(1)   | 177.6(14) |
| C(1)-Pt(1)-N(4)   | 95.6(14)  |
| N(1)-Pt(1)-N(4)   | 86.8(10)  |
| C(1)-Pt(1)-N(5)   | 93.8(14)  |
| N(1)-Pt(1)-N(5)   | 86.0(10)  |
| N(4)-Pt(1)-N(5)   | 89.6(11)  |
| N(6)-B(1)-N(2)    | 107(2)    |
| N(6)-B(1)-N(3)    | 107(2)    |
| N(2)-B(1)-N(3)    | 104(2)    |
| C(2)-N(1)-N(2)    | 107(2)    |
| C(2)-N(1)-Pt(1)   | 136(2)    |
| N(2)-N(1)-Pt(1)   | 117.2(16) |
| C(4)-N(2)-N(1)    | 104(2)    |
| C(4)-N(2)-B(1)    | 131(3)    |
| N(1)-N(2)-B(1)    | 123(2)    |
| C(7)-N(3)-N(4)    | 108(2)    |
| C(7)-N(3)-B(1)    | 134(2)    |
| N(4)-N(3)-B(1)    | 118(2)    |
| C(5)-N(4)-N(3)    | 100(3)    |
| C(5)-N(4)-Pt(1)   | 141(3)    |
| N(3)-N(4)-Pt(1)   | 118(2)    |
| C(10)-N(5)-N(6)   | 111(3)    |
| C(10)-N(5)-Pt(1)  | 136(3)    |
| N(6)-N(5)-Pt(1)   | 112(2)    |
| N(5)-N(6)-C(8)    | 109(2)    |
| N(5)-N(6)-B(1)    | 130(3)    |
| C(8)-N(6)-B(1)    | 122(3)    |
| C(3)-C(2)-N(1)    | 110(2)    |
| C(2)-C(3)-C(4)    | 108(3)    |
| N(2)-C(4)-C(3)    | 111(3)    |
| N(4)-C(5)-C(6)    | 111(3)    |
| C(7)-C(6)-C(5)    | 110(3)    |
| C(6)-C(7)-N(3)    | 110(3)    |
| C(9)-C(B)-N(6)    | 99(3)     |
| C(10)-C(9)-C(8)   | 115(4)    |
| C(9)-C(10)-N(5)   | 107(3)    |
| C(11)-Pt(2)-N(9)  | 91(2)     |
| C(11)-Pt(2)-N(11) | 96(2)     |
| N(9)-Pt(2)-N(11)  | 84.0(8)   |
| C(11)-Pt(2)-N(7)  | 177(2)    |
| N(9)-Pt(2)-N(7)   | 88.1(9)   |
| N(11)-Pt(2)-N(7)  | 86.7(9)   |
| N(10)-B(2)-N(12)  | 105(2)    |
| N(10)-B(2)-N(8)   | 104(2)    |
| N(12)-B(2)-N(8)   | 102(2)    |
| C(14)-N(7)-N(8)   | 110(3)    |
| C(14)-N(7)-Pt(2)  | 136(2)    |
| N(8)-N(7)-Pt(2)   | 113.8(17) |
| N(7)-N(8)-C(12)   | 107(2)    |
| N(7)-N(8)-B(2)    | 130(2)    |
| C(12)-N(8)-B(2)   | 123(2)    |
| C(17)-N(9)-N(10)  | 105(2)    |
| C(17)-N(9)-Pt(2)  | 138(2)    |
| N(10)-N(9)-Pt(2)  | 116.0(16) |
| C(15)-N(10)-N(9)  | 111(2)    |
| C(15)-N(10)-B(2)  | 124(2)    |
| N(9)-N(10)-B(2)   | 125(2)    |
| N(12)-N(11)-C(20) | 108(2)    |
| N(12)-N(11)-Pt(2) | 116.0(16) |
| C(20)-N(11)-Pt(2) | 135(2)    |
| N(11)-N(12)-C(18) | 107(2)    |

TABLE 3-continued

Bond lengths [A] and angles [deg] for complex 1

| | |
|---|---|
| N(11)-N(12)-B(2) | 126(2) |
| C(18)-N(12)-B(2) | 127(2) |
| C(13)-C(12)-N(8) | 108(3) |
| C(14)-C(13)-C(12) | 101(3) |
| N(7)-C(14)-C(13) | 113(3) |
| N(10)-C(15)-C(16) | 98(3) |
| C(17)-C(16)-C(15) | 116(4) |
| C(16)-C(17)-N(9) | 110(3) |
| C(19)-C(16)-N(12) | 107(3) |
| C(20)-C(19)-C(18) | 112(3) |
| C(19)-C(20)-N(11) | 105(3) |

Figure 5:
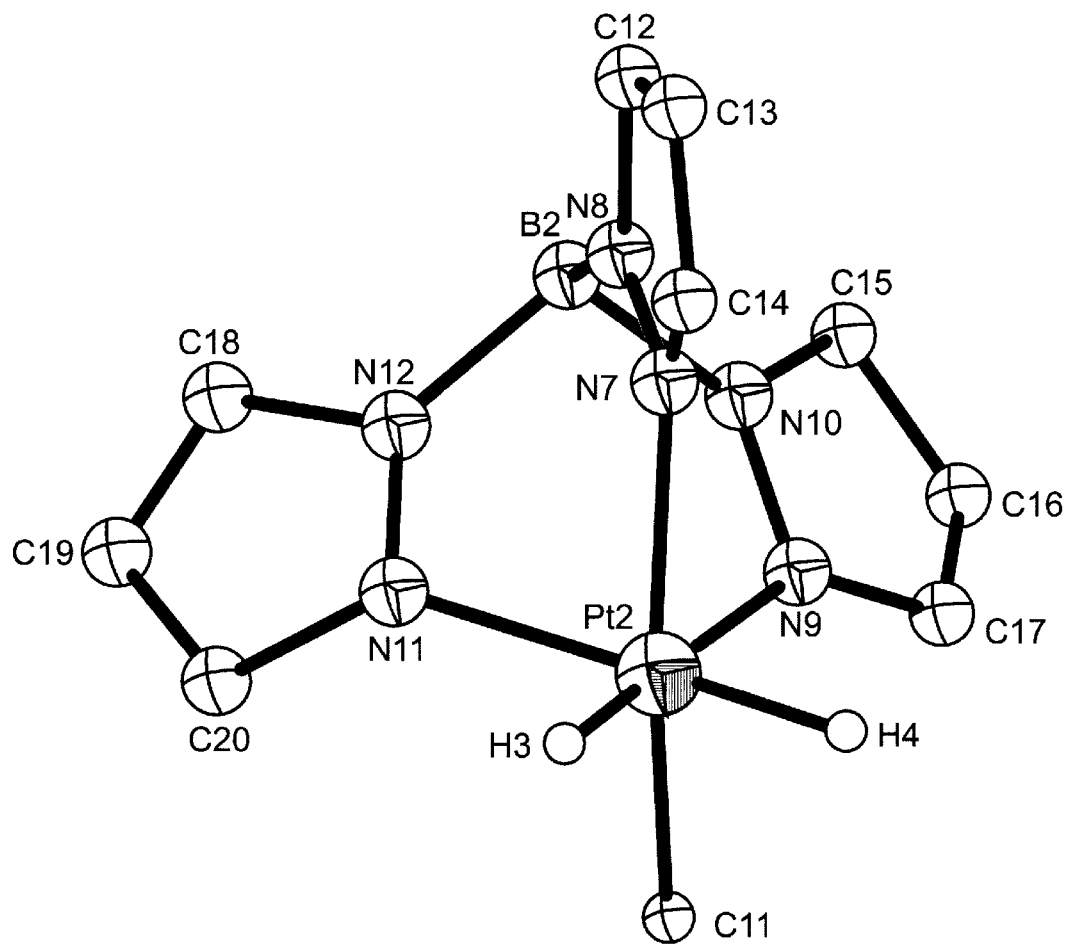
FIG. 5 presents the molecular structure of complex 1, with the adopted atom numbering. Only one of the two complex 1 molecules forming the cell unit is shown.

As is shown in FIG. 5, the x-ray analysis revealed four ligands positioned around the Pt(IV) center, leaving two empty sites, which, based on the spectroscopic analysis, are a pair of hydride ligands. Therefore, in FIG. 5 only the theoretical position of the non-located hydride ligands are shown.

However a strong support to the proposed structural of complex 1 is derived from the finding that the three Pt-N bonds are very close in length (Pt2—N9=2.19(2) Angstrom, Pt2—N11=2.20(2) Angstrom, Pt2—N7=2.20(2) Angstrom). This implies that the trans effect of the three opposite ligands to the pyrazolyl rings are almost the same. That is known to be the case when comparing the trans effect of methyl and hydride ligands. Thus, one can conclude, based on the solid state and spectroscopic analysis that the two empty coordination sites in the solid state of complex 1 are filled by hydride ligands.

Example 8

Stability of Complex 1 in Solution

The activation of hydrocarbons (e.g. alkanes, alkenes, alkynes, arenes) and the reduction of organic molecules and water for the production of valuable chemicals is of major industrial importance. For example, methane is the major naturally occurring alkane broadly used in the so-called Shilov $^2$ process to produce methanol, as follows:

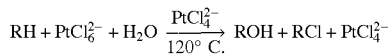

However, since the use of concentrated acid and high temperature are required in the above process, there is a great need for low temperature, natural pH catalysis.

The potential use of complex 1 as a catalyst for hydrocarbon C—H and C—C bond activation is apparent to those skilled in the art due to its stability in solution.

$^1$H-NMR analysis revealed that the $Pt^{IV}$-H and $Pt^{IV}$-Me signals disappeared completely in an independent fashion only after 4 and 8 hours, respectively, to produce a yet uncharacterized mer (e.g., dimer-polymer). Addition of water to the acetone solution substantially slowed this degradation processes, indicating the formation of stabilizing hydrogen bonds between the hydride ligands and water protons.

The degradation of complex 1 in solution clearly shows the existence of a fluxional system therein.

Example 9

Degradation of Complex 1 in Solution Yields Additional Platinum Complexes

To achieve a better understanding of Complex 1 degradation in the process of hydrocarbon C—H and C—C bond activation, complex 1 was reacted for several days at 25° C. with 10 equivalents of acetic acid in an acetone solution, which resulted in the production of novel platinum complexes and their intermediates. $^1$H-NMR time-dependence experiments uncovered a dynamic process in which the formation and disappearance of platinum intermediates bearing new methyl and hydride ligands together with the formation of two platinum-based products.

It will be appreciated that the disappearance and formation of so many signals relating to several platinum complexes together with a formation of singlets at 5.56 and 0.67 ppm indicative of the 1H-NMR chemical shift of dihydrogen and methane, makes complex 1 of the present invention a good candidate for the activation of hydrocarbons and reduction of organic molecules and water.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications mentioned in this specification are herein incorporated in their entirety by reference into the specification, to the same extent as if each individual publication was specifically and individually indicated to be incorporated herein by reference. In addition, citation or identification of any publication in this application shall not be construed as an admission that such publication is available as prior art to the present invention.

REFERENCES CITED HEREINABOVE:

1. Arndtsen, B. A.; Bergman, R. G.; Mobley, T. A.; Peterson, T. H. Acc. Chem. Res. 1995, 28, 154.
2. Shilov, A. E.; Shulpin, G. B. Chem. Rev. 1997, 97, 2879. (b) Stahl, S. S.; Labinger, J. A.; Bercaw, J. E. Angew. Chem., Int. Ed. Engl. 1998, 37, 2180. (c) Bengali, A. A.; Arndtsen, B. A.; Burger, P. M.; Schultz, R. H.; Weiller, B. H.; Kyle, K. R.; Moore, C. B.; Bergman, R. G. Pure Appl. Chem. 1995, 67, 281. (d) Crabtree, R. H. Chem Rev. 1995, 95, 987. (e) Wick, D. D.; Goldberg, K. I. J. Am. Chem. Soc. 1997, 119, 10235. (f) Johansson, L.; Ryan, O. B., Tilset, M. J. Am. Chem. Soc. 1999, 121, 1974. (g) Holtcamp, M. W.; Labinger, J. A.; Bercaw, J. E. J. Am. Chem. Soc. 1997, 119, 848.
3. Appleton, T. G.; Hall, J. R; Neale, D. W.; Williams, M. A. J. Organomet. Chem. 1984, 276, C73. (b) Canty, A. J.; Honeyman, R. T.; Roberts, A. S.; Traill, P. R. J. Organomet. Chem. 1994, 471, C8. (c) Canty, A. J.; Fritsche, S. D.; Jin, H.; Skelton, B. W.; White, A. H. J. Organomet. Chem. 1995, 490, C18. (d) Canty, A. J.; Fritsche, S. D.; Jin, H.; Honeyman, R. T.; Skelton, B. W.; Wite, A. H. J. Organomet. Chem. 1996, 510, 281.
4. Monaghan, P. K.; Puddephatt, R. J. Organometallics 1984, 3, 444. A more recent report: (b) Rostovtsev, V. V.; Labinger, J. A.; Bercaw, J. E.; Lasseter, T. L.; Goldberg, K. I. Organometallics 1998, 17, 4350, argues against the validity of the results presented in reference 4a and suggests that the formation of Pt(IV)hydroxo complexes arises from air oxidation.
5. Anderson, D. W. W.; Ebsworth, E. A. A. V.; Rankin, D. W. H. J. Chem. Soc. Dalton Trans. 1973, 854. (b) Blacklaws, I. M.; Ebsworth, E. A. A. V.; Rankin, D. W. H.; Robertson, H. E. J. Chem. Soc. Dalton Trans. 1978, 753. (c) Blacklaws, I. M.; Brown, L. C.; Ebsworth, E. A. A. V.; Reed, F. J. S. J. Chem. Soc. Dalton Trans. 1978, 877. (d) Falk, C. D.; Halpern, J. J. Am. Chem. Soc. 1965, 87, 3523.
6. Lunistra, G. A.; Wang, S. S.; Stahl, S. S.; Labinger, J. A.; Bercaw, J. E. J. Organomet. Chem. 1995, 504, 75. (b)

Stahl, S. S.; Labinger, J. A.; Bercaw, J. E. *J. Am. Chem. Soc.* 1996, 5961. (c) Holtcamp, M. W.; Henling, L. M.; Day, M. W.; Labinger, J. A.; Bercaw, J. E. *Inorg. Chim. Acta*, 1998, 270, 467.

7. Stahl, S. S.; Labinger, J. A.; Bercaw, J. E. *Inorg. Chem.* 1998, 37, 2422.
8. Clark, H. C.; Manzer, L. E. *Inorg. Chem.* 1974, 13, 1996.
9. Anal: Calcd for $C_{10}H_{15}BN_6Pt$, C, 28.24; H, 3.53; N, 19.77. Found: C, 28.39; H, 3.40; N, 19.89.
10. TpPtMeH$_2$ of 1: $^1$H-NMR (acetone-d$_6$/D$_2$O (9:1), δ): 7.89 (d, 2H, $^3J_{H\text{-}H}$=2.2 Hz, H-5), 7.86 (d, 1H, $^3J_{H\text{-}H}$=2.2, H-5') 7.75 (d, 2H, $J_{H\text{-}H}$=2.2, $^3J_{Pt\text{-}H}$=8.4 Hz, H-3), 7.64 (d, 1H, $^3J_{H\text{-}H}$=2.2, $^3J_{Pt\text{-}H}$=8.8 Hz, H-3'), 6.30 (t, 2H, $^3J_{H\text{-}H}$=2.2, H-4), 6.24 (t, 1H, $^3J_{H\text{-}H}$=2.2, H4'), 1.04 (s, 3H, $^2J_{Pt\text{-}H}$=65.4 Hz, CH$_3$), −20.04 (s, 3H, $^1J_{Pt\text{-}H}$=1276 Hz, Pt-H). IR of 1 (KBr): 2253.2 ($\nu_{Pt\text{-}H}$), 2470.9 (br, $\nu_{B\text{-}H}$) cm$^{-1}$.
11. Hamilton, D. G.; Crabtree, R. H. *J. Am. Chem. Soc.* 1988, 110, 4126. (b) Crabtree, R. H. *Angew. Chem. Int. Ed. Engl.* 1993, 32, 789.
12. The $^{13}$C NMR signal (−30.4 ppm) of the Me-Pt is remarkably high compared with other reported TpPt(IV) methyl complexes where the methyl absorbs at −19.62 and −3.69 ppm (reference 25b).
13. TpPtMeH$_2$ (1): $^{13}$C-NMR (acetone-d$_6$/D$_2$O, 9:1): 144.5 (s, $^2J_{Pt\text{-}C}$=35.3 Hz, 1C, C3'), 141.0 (s, $^2J_{Pt\text{-}C}$=27.3 Hz, 2C, C3), 136.0 (br, 3C, C5/C5'), 106.9 (s, $^3J_{Pt\text{-}C}$=19.2 Hz, 1C, C4'), 106.7 (s, $^3J_{Pt\text{-}C}$=16.05Hz, 2C, C4), −30.4 (s, $^1J_{Pt\text{-}C}$=561.5 Hz, 3C, CH$_3$).
14. An intense Pt-H stretch signal has been reported in reference 5a.
15. Edgell, W. F.; Summit, R. *J. Am. Chem Soc.* 1961, 83, 1772.
16. Spencer, A. In Comprehensive Coordination Chemistry; Wilkinson, G. Ed; Pergamon; Oxford, V. K., 1987, 6, 292. (b) Cheng, C-H.; Eisenberg, R. *J. Am. Chem. Soc.* 1978, 100, 5968. (c) Clark, H. C.; Jain, V. K. *Coord. Chem. Rev.* 1984, 55, 151. (d) Holt, M. S.; Wilson, W. L.; Nelson, J. H. *Chem. Rev.* 1989, 89, 11.
17. Manzer, L. E.; Meakin, P. Z. *Inorg. Chem.* 1976, 15, 3117.
18. Rush, P. E.; Oliver, J. D. *J. Chem. Soc. Chem. Comm.* 1974, 996. (b) Rush, P. E.; Oliver, J. D. *J. Organomet. Chem.* 1976, 104, 117.
19. $^1$H-NMR data of 2: (CDCl$_3$, rt): 7.68 (br, 3H, H3/H3' or H5/H5'), 7.49 (br, 3H, H5/H5' or H3/H3'), 6.30 (br, 3H, H4/H4'), 1.02 (s, 3H, $^2J_{Pt\text{-}H}$=70.2 Hz, CH$_3$).
20. $^{13}$C-NMR of 2 (CDCl$_3$, −40° C.): 164.7 (s, 1C, CO), 142.4 (s, 1C, $^2J_{Pt\text{-}C}$=37.5 Hz, C3'), 140.9 (s, $^2J_{Pt\text{-}C}$=34.4 Hz, 2C, C3), 136.3 (s, 1C, C5'), 135.9 (s, 2C, C5), 106.5 (s, 1C, C4'), 105.3 (s, 2C, C4), −17.7 (s, $^1J_{Pt\text{-}C}$=524.6 Hz, 3C, CH$_3$).
21. Northcutt, T. O.; Lachicotte, R. J.; Jones, W. D. *Organometallics* 1998, 17, 5148.
22. Akita, M.; Ohta, K.; Takahashi, Y.; Hikichi, S.; Moro-oka, Y. *Organometallics* 1997, 16, 4121.
23. Ziessel, R. *J. Am. Chem. Soc.* 1993, 115, 118. (b) Miller, R. G.; Kyle, J. A.; Coates, G. W.; Anderson, D. J.; Fanwick, P. E. *Organometallics* 1993, 12, 1161.
24. Canty, A. J.; Dedieu, A.; Jin, H.; Milet, A.; Richmond, M. K. *Organometallics* 196, 15, 2845. (b) Canty, A. J.; Fritsche, S. D.; Jin, H.; Patel, J.; Skelton, B. W.; White, A. H. *Organometallics* 1997, 16, 2175.
25. O'Reilly, S. A.; White, P. S.; Templeton, J. L. *J. Am. Chem. Soc.* 199, 118, 5684.
26. De Felice, V.; De Renzi, A.; Panunzi, A.; Tesauro, D. *J. Organomet. Chem.* 1995, 488, C13. (b) Stahl, S. S.; Labinger, J. A.; Bercaw, J. E. *J. Am. Chem. Soc.* 1995, 117, 9371. (c) Hill, G. S.; Rendina, L. M.; Puddephatt, R. J. *Organometallics* 1995, 14, 4966. (d) Hill, G. S.; Puddephatt, R. J. *J. Am. Chem. Soc.* 1996, 118, 8745. (e) Jenkins, H. A.; Yap, G. P. A.; Puddephatt, R. J. *Organometallics* 1997, 16, 1946.
27. $^1$H-NMR data of 3: (D$_2$O-acetone-d$_6$, 1:1): 8.08 (d, $^3J_{H\text{-}H}$=2.2 Hz, 1H, H3' or H5'), 8.02 (d, $^3J_{H\text{-}H}$=2.2 Hz, 2H, H3 or H5), 7.96 (d, $^3J_{H\text{-}H}$=22 Hz, 1H, H5' or H3'), 7.86 (d, $^3J_{H\text{-}H}$=2.2 Hz, 2H, H5 or H3), 6.61 (t, $^3J_{H\text{-}H}$=2.2 Hz, 2H, H4), 6.55 (t, $^3J_{H\text{-}H}$=2.2 Hz, 1H, H4'), 0.85 (s, 3H, $^2J_{Pt\text{-}H}$=70.6 Hz, CH$_3$). $^{19}$F-NMR (acetone, external standard: Bu$_4$N$^+$ PF$_6^-$) −57.24 ppm (s). Anal: Calcd for $C_{11}H_{14}B_2F_4N_6OPt$, C, 24.50; H, 2.60; N, 15.59; Found: C, 24.60; H. 2.74; N. 15.56.
28. Data were collected at 298° K. with a Siemens P4 diffractometer equipped with a molybdenum sealed tube and a highly oriented graphite monochromator. 3: Empirical Formula: $C_{11}H_{13}B_2F_4N_6OPt$, Formula Weight= 537.98, colorless plate, monoclinic, space group=P2$_1$/c, a=11.915 (1) Angstrom, b=12.0221 (1) Angstrom, c=24.628 (2) Angstrom, α=90°, β=93.52° (1), γ=90°, V=3491.6 (5) Angstrom$^3$, Z=8, R$_1$=0.0795 [I>2σ(I)], GOF=1.011. The observation that Z=8 in the space group P2$_1$/c suggests that the asymmetric unit cell consists of two independent molecules. The solid state structure of 3 provides mainly atom connectivity in the molecule due to the substantial disorder in the counter-anion and in the CO and CH$_3$ ligands.
29. A cis-dihydrido(bisphosphine)platinum(IV) complex was recently characterized by X-ray crystallography: Edelbach, B. L.; Vicic, D. A.; Lachicotte, R. J.; Jones, W. D. *Organometallics* 1998, 17, 4784.

What is claimed is:

1. A solution comprising a solvent and a platinum complex therein in which a platinum(IV) metal center is complexed in cis orientations with two hydride groups and with an alkyl group.

2. The solution of claim 1, wherein said platinum complex includes a complexing ligand selected from the group consisting of hydridotris(pyrazolyl)borate hydridotris (pyrazolyl) borate, hydridotris(pyrazolyl) methane, aryltris (pyrazolyl) borate, aryltris(pyrazolyl) methane. heteroaryltris(pyrazolyl) borate, heteroaryltris(pyrazolyl) methane. alkyltris(pyrazolyl) borate and substituents thereof.

3. The solution of claim 1, wherein said solvent includes at least one substance selected from the group consisting of water, a hydrocarbon, an alcohol, a ketone and an organic acid.

4. The solution of claim 3, wherein said hydrocarbon is selected from the group consisting of an alkane, an alkene, an alkyne and an arene.

5. A platinum complex comprising a platinum(IV) metal center so positioned and oriented in the complex so as to complex in cis orientations with two hydride groups and with an alkyl group.

6. The platinum complex of claim 5, further comprising a complexing ligand selected from the group consisting of hydridotris(pyrazolyl) borate, hydridotris(pyrazolyl) methane, aryltris(pyrazolyl) borate, aryltris(pyrazolyl) methane, heteroaryltris(pyrazolyl) borate, heteroaryltris (pyrazolyl) methane and alkyltris(pyrazolyl) borate.

7. The platinum complex of claim 5, wherein the complex is in a solid state.

8. The platinum complex of claim 5, wherein the complex is in a dissolved state.

9. A method of preparing a platinum complex including a platinum(IV) metal center so positioned and oriented so as to complex in cis orientations with two hydride groups and with an alkyl group, the method comprising the step of contacting platinum complex including a platinum(II) metal center being complexed with a CO group and the alkyl group with water to thereby obtain said platinum complex including said platinum(IV) metal center so positioned and oriented so as to complex in cis orientations with said two hydride groups and with said alkyl group.

10. The method of claim 9, wherein said platinum complex including said platinum(II) metal center complexed with said CO group and said alkyl group includes a complexing ligand selected from the group consisting of hydridotris(pyrazolyl) borate, hydridotris(pyrazolyl) methane, aryltris(pyrazolyl) borate, aryltris(pyrazolyl) methane, heteroaryltris(pyrazolyl) borate, heteroaryltris(pyrazolyl) methane and alkyltris(pyrazolyl) borate.

11. A process of activating a C—C bond of a hydrocarbon, the process comprising the step of contacting the hydrocarbon with a platinum complex including a platinum(IV) metal center so positioned and oriented in the complex so as to complex in cis orientations with two hydride groups and with an alkyl group, thereby activating said C—C bond of said hydrocarbon.

12. The process of claim 11, wherein said platinum complex includes a complexing ligand selected from the group consisting of hydridotris(pyrazolyl) borate, hydridotris(pyrazolyl) methane, aryltris(pyrazolyl) borate, aryltris(pyrazolyl) methane, heteroaryltris(pyrazolyl) borate, heteroaryltris(pyrazolyl) methane and alkyltris(pyrazolyl) borate.

13. The process of claim 11, wherein said solution includes at least one substance selected from the group consisting of water, an alcohol, a ketone, an aldehyde and an organic acid.

14. The process of claim 11, wherein said hydrocarbon is selected from the group consisting of an alkane, an alkene, an alkyne and an arene.

15. A process of activating a C—H bond of a hydrocarbon, the process comprising the step of contacting the hydrocarbon with a platinum complex including a platinum(IV) metal center so positioned and oriented in the complex so as to complex in cis orientations with two hydride groups and with an alkyl group, thereby activating said C—H bond of said hydrocarbon.

16. The process of claim 15, wherein said platinum complex includes a complexing ligand selected from the group consisting of hydridotris(pyrazolyl) borate, hydridotris(pyrazolyl) methane, aryltris(pyrazolyl) borate, aryltris(pyrazolyl) methane, heteroaryltris(pyrazolyl) borate, heteroaryltris(pyrazolyl) methane and alkyltris(pyrazolyl) borate.

17. The process of claim 15, wherein said hydrocarbon and said complex are in solution, said solution includes at least one substance selected from the group consisting of water, an alcohol, a ketone, an aldehyde and an organic acid.

18. The process of claim 15, wherein said hydrocarbon is selected from the group consisting of an alkane, an alkene, an alkyne and an arene.

19. A process of reducing an organic molecule or water, the process comprising the step of contacting the organic molecule or water with a platinum complex including a platinum(IV) metal center so positioned and oriented in the complex so as to complex in cis orientations with two hydride groups and with an alkyl group, thereby reducing the organic molecule or water.

* * * * *